US008512998B2

(12) United States Patent
Clayton et al.

(10) Patent No.: US 8,512,998 B2
(45) Date of Patent: Aug. 20, 2013

(54) PROCESS FOR MICROALGAE CONDITIONING AND CONCENTRATION

(75) Inventors: Robert L. Clayton, Tuscon, AZ (US); Stephen N. Falling, Kingsport, TN (US); Jeffrey S. Kanel, Kingsport, TN (US)

(73) Assignees: Renewable Algal Energy, LLC, Kingsport, TN (US); Eastman Chemical Company, Kingsport, TN (US)

( * ) Notice: Subject to any disclaimer, the term of this patent is extended or adjusted under 35 U.S.C. 154(b) by 392 days.

(21) Appl. No.: 12/665,218

(22) PCT Filed: Jun. 18, 2008

(86) PCT No.: PCT/US2008/007664
§ 371 (c)(1),
(2), (4) Date: Dec. 17, 2009

(87) PCT Pub. No.: WO2008/156819
PCT Pub. Date: Dec. 24, 2008

(65) Prior Publication Data
US 2010/0167339 A1 Jul. 1, 2010

Related U.S. Application Data

(60) Provisional application No. 60/944,813, filed on Jun. 19, 2007.

(51) Int. Cl.
*C12N 1/12* (2006.01)
(52) U.S. Cl.
USPC ......... 435/257.1; 435/259; 435/260; 435/261

(58) Field of Classification Search
None
See application file for complete search history.

(56) References Cited

U.S. PATENT DOCUMENTS

| | | |
|---|---|---|
| 3,428,175 A | 2/1969 | Hukki |
| 3,730,341 A | 5/1973 | Mames et al. |
| 3,802,569 A | 4/1974 | Nagahama |
| 3,875,052 A | 4/1975 | Lonchamp et al. |
| 3,951,805 A | 4/1976 | Dodd |
| 4,021,303 A | 5/1977 | Nakabayashi |
| 4,055,491 A | 10/1977 | Porath-Furedi |
| 4,115,949 A | 9/1978 | Avron et al. |
| 4,186,094 A | 1/1980 | Hellberg |
| 4,203,837 A | 5/1980 | Hoge et al. |

(Continued)

FOREIGN PATENT DOCUMENTS

| AU | 2002101010 | 5/2003 |
|---|---|---|
| DE | 3101221 | 8/1982 |

(Continued)

OTHER PUBLICATIONS

Chisti et al., Enzyme Microb. Technol., 1986, vol. 8, p. 194-204.*

(Continued)

*Primary Examiner* — Kade Ariani
(74) *Attorney, Agent, or Firm* — Phan Law Group PLLC

(57) ABSTRACT

Conditioning and concentration of microalgae are accomplished by the process steps of grinding a dilute aqueous dispersion of microalgae in the presence of grinding media and then applying adsorptive bubble separation. This process is amenable to the use of dilute feed microalgal dispersions such as are encountered in the production of algal biomass for biofuel applications.

12 Claims, 5 Drawing Sheets

(56) References Cited

U.S. PATENT DOCUMENTS

| | | |
|---|---|---|
| 4,288,319 A | 9/1981 | Heijs et al. |
| 4,341,630 A | 7/1982 | Mackrle et al. |
| 4,399,028 A | 8/1983 | Kile et al. |
| 4,425,232 A | 1/1984 | Lawrence et al. |
| 4,554,390 A | 11/1985 | Curtain et al. |
| 4,668,382 A | 5/1987 | Jameson |
| 4,680,314 A | 7/1987 | Nonomura |
| 4,735,709 A | 4/1988 | Zipperian |
| 4,800,017 A | 1/1989 | Krishnaswamy et al. |
| 4,931,291 A | 6/1990 | Kojima et al. |
| 4,938,865 A | 7/1990 | Jameson |
| 4,981,582 A | 1/1991 | Yoon et al. |
| 5,022,984 A | 6/1991 | Pimley et al. |
| 5,078,921 A | 1/1992 | Zipperian |
| 5,167,798 A | 12/1992 | Yoon et al. |
| 5,167,806 A | 12/1992 | Wang et al. |
| 5,188,726 A | 2/1993 | Jameson |
| 5,205,926 A | 4/1993 | Lawrence |
| 5,240,600 A | 8/1993 | Wang |
| 5,251,764 A | 10/1993 | Niiti et al. |
| 5,330,913 A | 7/1994 | Nakayama |
| 5,332,100 A | 7/1994 | Jameson |
| 5,374,522 A | 12/1994 | Murphy et al. |
| 5,382,358 A | 1/1995 | Yeh |
| 5,431,286 A | 7/1995 | Xu et al. |
| 5,490,924 A | 2/1996 | Macia et al. |
| 5,626,767 A | 5/1997 | Trampler et al. |
| 5,651,879 A | 7/1997 | Gonzalez |
| 5,776,349 A | 7/1998 | Guelcher et al. |
| 5,897,772 A | 4/1999 | Chiang et al. |
| 5,910,254 A | 6/1999 | Guelcher et al. |
| 5,951,875 A * | 9/1999 | Kanel et al. .................. 210/703 |
| 6,000,551 A | 12/1999 | Kanel et al. |
| 6,080,320 A | 6/2000 | von Phul |
| 6,092,667 A | 7/2000 | Steinmuller et al. |
| 6,095,336 A | 8/2000 | Redden et al. |
| 6,328,165 B1 | 12/2001 | Baker et al. |
| 6,332,980 B1 | 12/2001 | Moorehead |
| 6,405,948 B1 | 6/2002 | Hahn et al. |
| 6,524,486 B2 | 2/2003 | Borodyanski |
| 6,589,785 B1 | 7/2003 | Mullner et al. |
| 6,832,690 B2 | 12/2004 | Kujawa |
| 7,108,136 B2 | 9/2006 | Imhof |
| 2003/0201232 A1 | 10/2003 | Cheyne |
| 2003/0209471 A1 | 11/2003 | Gabl |
| 2006/0084165 A1 | 4/2006 | Lee et al. |

FOREIGN PATENT DOCUMENTS

| | | |
|---|---|---|
| DE | 3634903 | 4/1988 |
| GB | 2114469 | 8/1983 |
| WO | 02/07890 | 1/2002 |
| WO | 2006056018 | 6/2006 |

OTHER PUBLICATIONS

Flotation Science and Engineering, pp. 1-44 (K.A. Mattis ed., 1995) Marcel Dekker, New York, NY.

Adsorptive Bubble Separation Techniques, pp. 1-5 (R. Lemlich ed., 1972) Academic Press, New York, NY.

G.V. Levin et al., "Harvesting of Algae by Froth Flotation," Applied and Environmental Microbiology, vol. 10, pp. 169-175 (1962).

Y. Christi, "Biodiesel from Microalgae," Biotechnology Advances, vol. 25, pp. 294-306 (2007).

"A Look Back at the U.S. Department of Energy's Aquatic Species Program: Biodiesel from Algae," NREL/ TP-580-24190, pp. 1-294 (1998).

Olaizola, M., "Commercial Development of Microalgal Biotechnology: From the Test Tube to the Marketplace," Biomolecular Eng., Elsevier, New York, NY, vol. 20, No. 4-6, pp. 459-466 (Jul. 1, 2003).

Molina, Grima E., et al., "Recovery of Microalgal Biomass and Metabolites: Process Options and Economics," Biotechnology Advances, Elsevier Publishing, Barking, GB, vol. 20, No. 7-8, pp. 491-515 (Jan. 1, 2003).

N. Barbian et al., "The froth stability column: Measuring froth stability at an industrial scale," Minerals Eng., vol. 19, pp. 713-718 (2006).

W. Phoochinda et al., "Removal of Algae Using Froth Flotation," Environmental Tech., vol. 24, pp. 87-96 (2003).

C.W. Schultz et al., "The flotation column as a froth separator," Mining Eng., pp. 1449-1451 (Dec. 1991).

A.K. Cowen et al., "Dunaliella salina: A model System for Studying the Response of Plant Cells to Stress," J. Exp. Botany, vol. 43, pp. 1535-1547 (1992) (Abstract only).

* cited by examiner

PROCESS FOR MICROALGAE CONDITIONING AND CONCENTRATION

REFERENCE TO RELATED APPLICATION

This application claims priority under 35 U.S.C. §119(e) to U.S. Provisional Patent application 60/944,813, filed on Jun. 19, 2007, the contents of the entirety of which are incorporated herein by this reference.

TECHNICAL FIELD

The invention relates generally to the field of algal utilization, such as in biofuels, and more particularly to a process for microalgae conditioning and/or concentration.

BACKGROUND

Microalgae are simple aquatic organisms that produce oxygen and organic matter by photosynthesis. Microalgae have uses in the production of food, nutritional supplements, pharmaceuticals, natural pigments, biochemicals, and biomass for fuel production. They have also utility in the removal of nitrogen, phosphorus and heavy metals in waste water. Microalgae are particularly useful because of their high growth rate and tolerance to various environmental conditions.

Due to the wide range of uses of microalgae and microalgae-based products, effective methods for growing and harvesting microalgae are essential. "Conditioning" is the treatment of an aqueous microalgae dispersion by cell rupture, chemical treatment, and/or flocculation in order to facilitate isolation of the microalgae or cellular components in a subsequent step.

Two basic approaches exist for the culture of microalgae: closed bioreactor systems and open pond systems. The most capital intensive system is the closed bioreactor which utilizes transparent conduits in which the microalgae grow in water by exposure to light and introduction of carbon dioxide and nutrients. Major reasons for choosing the bioreactor design are control of the culture and/or the desire to remove carbon dioxide from waste gas emissions. With a genetically-modified microalgal species, isolation helps to prevent contamination by other species and escape into the environment.

Harvested microalgae biomass can be converted to animal feed, solid fuel, methane, hydrogen, synthesis gas, or liquid transportation fuels such as biodiesel, and bioethanol. Sequential operations may allow production of two or more of these products from the microalgal lipids (triglycerides), starches and residues. Of special interest herein is the production of fatty acid esters (biodiesel) from the microalgal lipids. See, for example, the research review paper: "Biodiesel from microalgae," Yusuf Chisti, *Biotechnology Advances*, volume 25, pages 294-306 (2007), the contents of which are incorporated herein by this reference. Harvested microalgae biomass may also be hydrotreated for the production of liquid hydrocarbons.

The optimum population density for microalgae cultivation is one where light reaches the full depth of the growing medium, without upper layers substantially shading the lower. The range of 200,000 to 500,000 cells per milliliter is commonly used within the art as an efficient population density for growth of unicellular microalgae. In agitated ponds and bioreactors, higher populations can be maintained, while in static ponds, lower densities perform best. These population densities result in low concentrations (on the order of 0.02 weight percent) of microalgal products in the culture medium.

Pre-concentration of microalgae before harvesting is a desirable step in order to reduce the volume of microalgae culture handled. However, pre-concentration is difficult and expensive to implement in large scale aquaculture systems such as would be needed for microalgal biofuel production. Except in the production of very high-value microalgal products, current microalgae harvesting technology is uneconomical for handling the large volume of growth media. In order for microalgae to become an economical, renewable source of low-value, high-volume products (such as biofuels), improved methods for growing, harvesting, and concentrating microalgae are needed.

Numerous techniques have been tried for removing microalgae from a liquid stream. Filtration is the most common process for isolating solids from liquid dispersions and many configurations of filters have been used or attempted with microalgae. However many useful species of microalgae are not amenable to filtration due to their very small size and/or their soft, deformable structure which causes plugging of the filter. U.S. Pat. No. 5,490,924, the contents of which are incorporated herein by this reference, describes a filter system having a backwash and filter cleaning system adapted to simultaneously vertically-reciprocate and rotate to selectively dislodge microalgae and other particulates from the filter. This system is suitable for water purification, but not for large-scale microalgae biomass isolation. U.S. Pat. No. 3,875,052, the contents of which are incorporated herein by this reference, details a multi-step process which comprises a pre-concentration step in which the microalgae suspension is fed along a filtration surface at a high contact velocity, followed with filtration, washing and pressing. However this process is only amenable to filamentous microalgae and not to smaller, single-celled microalgae.

U.S. Pat. No. 6,328,165, the contents of which are incorporated herein by this reference, describes a harvesting apparatus for marine aquaculture which uses a complex moving belt filter and incorporates wash cycles.

U.S. Pat. No. 3,951,805, the contents of which are incorporated herein by this reference, is a complex and expensive belt filter device for harvesting microalgae. There are many more filtering techniques that can be utilized, but in all of them, particular attention must be paid to the clearing or cleaning of the filter to insure efficient operation. If the microalgae can deform, it can quickly plug or blind the filter.

Centrifugation is another common solids isolation technique which is sometimes cited for use in microalgae isolation. For example, U.S. Pat. No. 4,115,949, the contents of which are incorporated herein by this reference, describes the culture and centrifugation of microalgae for the production of glycerol and proteinaceous substances of nutritive value. Centrifugation, filtration, and sedimentation are methods of microalgae harvesting that were discussed in "A Look Back at the U.S. Department of Energy's Aquatic Species Program: Biodiesel from Algae," NREL/TP-580-24190 (1998), the contents of which are incorporated herein by this reference. Unfortunately centrifugation equipment is too expensive for the initial step of large-scale microalgae harvesting for low-cost, high-volume products.

U.S. Pat. No. 6,332,980, the contents of which are incorporated herein by this reference, describes the use of dissolved air flotation and a hydrocyclone separator to remove volatile gases, pesticides, and particles such as microalgae from water. This system is suitable for water purification but not for large-scale microalgae biomass isolation.

Acoustic energy has also been used to separate particles, including microalgae, from the carrier liquid. U.S. Pat. Nos. 4,055,491 and 5,626,767, the contents of each of which are incorporated herein by this reference, describe the use of an ultrasonic resonance wave to move particles, including microalgae, at different rates, allowing them to be separated. However, this technique relies on differences in the acoustic properties between the solid and the liquid, and since microalgae are occasionally neutrally buoyant, a large amount of energy would be required for the separation.

Harvesting microalgae on an adsorbent having a hydrophobic surface was disclosed by Curtain, et al. in U.S. Pat. No. 4,554,390, the contents of which are incorporated herein by this reference. This process is practical in the production of high value products but it is too expensive for biofuel applications.

Adsorptive bubble separations are a group of processes used in treating a feed dispersion that comprises a carrier liquid and hydrophobic material that is molecular, colloidal, and/or particulate in nature. This hydrophobic material is selectively collected (i.e., adsorbed or attached) to the surface of bubbles such that they can be allowed to rise through the carrier liquid, thereby concentrating or separating the hydrophobic material from the carrier liquid. The resulting froth with collected particles may be treated in one of several ways to collapse the froth and isolate the particles. This important process is commercially utilized in a wide range of applications that include isolation of minerals and metals from ore, dewatering of microalgae, removal of oil droplets from an aqueous stream, removal of ash particulates from coal, removal of particles in waste-water treatment streams, purification of drinking water, and removal of ink and adhesives during paper recycling. See for example, "Harvesting of Algae by Froth Flotation," G. V. Levin, et al., *Applied and Environmental Microbiology*, volume 10, pages 169-175 (1962), the contents of which are incorporated herein by this reference. Other applications of adsorptive bubble processes are described in *Adsorptive Bubble Separation Techniques*, Robert Lemlich, Editor, Academic Press, New York, N.Y. (1972) which is hereby incorporated by reference. In all of these applications, there is a need to efficiently contact particles or droplets in an aqueous dispersion with a gas and then attach the hydrophobic material to the bubbles. This process is amenable to very large feed streams and is widely practiced as such in the mining industry.

For adsorptive bubble processes to separate materials, hydrophobic materials comprise the component to be separated. Rendering material hydrophobic is commonly called "conditioning", wherein particle surfaces are treated with chemicals, or other techniques that selectively modify the component to be separated. In most cases, the particles are not initially hydrophobic, and the particles to be separated or dewatered are made hydrophobic so they may be collected and separated with an adsorptive bubble process. In other cases, the particles are all hydrophobic, and one component is modified to make it hydrophilic in order to keep it in the aqueous stream.

Microalgae are hydrophilic therefore adsorptive bubble separation is minimally effective on whole, live microalgae cells. In order to use adsorptive bubble separation, microalgae cells must be conditioned to make them hydrophobic.

An example of the use of flocculation conditioning followed by adsorptive bubble separation to harvest microalgae was disclosed in U.S. Pat. No. 4,680,314, the contents of which are incorporated herein by this reference. U.S. Pat. No. 6,524,486, the contents of which are incorporated herein by this reference, also utilizes a flocculating agent to cause accumulations of microalgae that are then floated out using an adsorptive bubble process. This process requires the addition of flocculating agents, which are expensive, may have environmental concerns, and can contaminate the product or the growth medium.

Another method to render the microalgae cells hydrophobic so as to use adsorptive bubble separation is by "cell rupture" (also referred to as "cell disruption" or "lysis"). By rupturing the cell wall and/or cell membrane, lipids and other naturally hydrophobic components are released from the cell. These components and cell fragments can then be recovered with an adsorptive bubble separation process.

Cell rupture can be achieved by a number of methods which can be classified as chemical, physical or mechanical. The chemical methods include enzymatic digestion, detergent solubilization, lipid dissolution with a solvent, and alkali treatment (lipid saponification). Physical methods include osmotic shock, decompression, sonication, heat treatment, and freeze-thawing. Mechanical methods include grinding, high shear homogenization and pressure extrusion. High speed impeller homogenization of cells (e.g., kitchen blender) is a mechanically simple process, but requires high energy and heat removal. The large energy requirement per volume of microalgal media renders this technique uneconomical for large-scale aquaculture systems. See for example, U.S. Pat. No. 4,931,291, the contents of which are incorporated herein by this reference, which uses various microalgal cell rupture methods to produce feed for crustacean and shellfish larvae.

A common cell disruption process in the prior art uses a pump to force the feed mixture at high pressure through a restricted orifice valve. Cell disruption is accomplished by three different mechanisms: impingement on the valve, high liquid shear in the orifice, and sudden pressure drop upon discharge, causing finally an explosion of the cell. As an example of this, the MICROFLUIDIZER™ cell disruption equipment of Microfluidics, Newton, Mass., US utilizes pressures of about 5,000 to 40,000 prig (345-2760 bar). U.S. Pat. No. 6,405,948, the contents of which are incorporated herein by this reference, describes a method for liberating intracellular materials using a resonance disintegration mill in which a high speed rotor creates a series of compressions and decompressions.

U.S. Pat. Nos. 5,776,349 and 6,000,551, the contents of which are incorporated herein by this reference, disclose that microalgae cells are ruptured when the microalgal feed dispersion is subjected to a pressure drop created by pumping through an orifice. Pressure drops of 50 to 200 psig (3.4-14 bar) are claimed to render an acceptable percentage of the cells recoverable with an adsorptive bubble separation. However, it is expensive to pump the entire feed dispersion, where the growing media may represent greater than 99% of the mass, at these pressures to obtain a high percentage of cell rupture.

Fine grinding technology has application to microorganism cell disruption at the laboratory scale. In ball or bead mills, cells are agitated in suspension with grinding media which are small abrasive particles such as glass or ceramic beads. Cells break because of shear forces, grinding between beads, and collisions with the beads. U.S. Pat. No. 5,330,913, the contents of which are incorporated herein by this reference, claims that an aqueous suspension of *Chlorella* cells is disrupted by the rapid pressure changes created by a rotating impeller within a small, cylindrical, tight-sealed container with rigid spheres having a constant diameter of 500 to 800 microns.

Horizontal or vertical, high-energy, disk mills employ a chamber containing disks on a high speed rotor and grinding media. The grinding process may be done batch-wise or continuously. This design is used for grinding pigments, dyes, pharmaceuticals, food products, minerals, and small quantities of biological cells.

U.S. Pat. No. 6,589,785, the contents of which are incorporated herein by this reference, describes a method of disrupting cells by freezing them into solids and fracturing them with a vibratory ball mill in the presence of denaturing substances. In the example cited, a device called the DISMEMBRATOR U was used to fracture small amounts of the cells. Any process requiring freezing the feed would be prohibitively expensive.

U.S. Pat. No. 5,374,522, the contents of which are incorporated herein by this reference, claims a method for rupturing microorganisms by the use of ultrasonic energy in the presence of small beads. U.S. Patent Application 2006/0084165, the contents of which are incorporated herein by this reference, describes a method of disrupting cells or viruses. The method involves adding magnetic beads to a solution containing cells or viruses, vibrating the magnetic beads and irradiating a laser upon the magnetic beads to disrupt the cells. Once again, these techniques are difficult and expensive to implement in large scale aquaculture systems such as would be needed for algal biofuel production.

SUMMARY OF THE INVENTION

Described are methods of concentrating microalgal biomass by disrupting aqueous dispersions of microalgae cells by grinding followed by adsorptive bubble separation. Microalgal cell disruption may be achieved by intimately contacting the microalgae and the grinding media in a grinding apparatus. The grinding apparatus may be, e.g., a vibratory grinding mill, agitated bead mill (stirred media mill) or a sonication chamber containing grinding media. The disrupted ("conditioned") microalgal suspension, when fed to an adsorptive bubble separation apparatus, produces a concentrated microalgal biomass stream and a stream depleted in microalgal biomass ("tails"). The microalgal biomass stream is sufficiently concentrated for further processing by centrifugation, pressing, extraction, and/or drying. By the methods disclosed herein, dilute microalgal suspensions from bioreactor or open pond production can be economically concentrated for use in the production of biofuels or other useful products. The process may also be useful in water purification or remediation of natural waterways contaminated by microalgal populations.

DETAILED DESCRIPTION OF THE INVENTION

Figure 1:
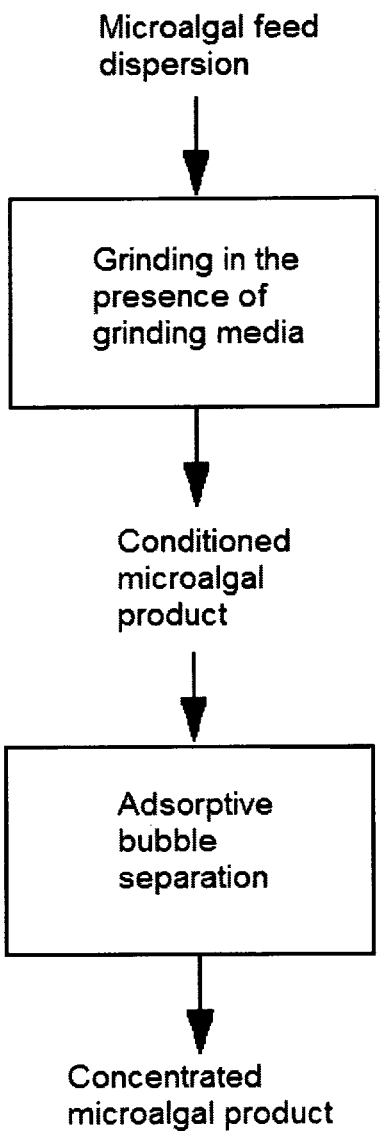
FIG. 1 is a block diagram of the invention showing the steps for conditioning a microalgal feed dispersion followed by adsorptive bubble separation.

Described are processes for concentrating microalgal biomass by disrupting microalgae cells by grinding followed by adsorptive bubble separation. In such processes, the aqueous microalgae feed dispersion is first passed through a grinding mill. The microalgae feed dispersion consists of a carrying liquid and the microalgae cells. The carrying liquid may be water, brine, seawater, aqueous solutions, growing media for the microalgae or reagents or a combination of any of these. The carrying liquid may contain nitrogen, phosphorous, iron, and other fertilizers used in the art. The microalgae feed dispersion can be supplied directly from a growing area or from a preceding process. This growing area can be natural or cultivated. The microalgae can be grown in open ponds or in bioreactors. Naturally occurring or other microalgal blooms may serve as the source of the feed dispersion. Some processes can pre-concentrate the microalgae within the growing area, thus reducing the volume to be conditioned, and thus the costs.

The microalgae can be any species of microalgae one desires to separate from the carrying liquid. These species include, but are not limited to Anabaena, Ankistrodesmus falcatus, Botryococcus braunii, Chaetoceros gracilis, Chlamydomonas reinhardtii, Chlorella vulgaris, Chlorella pyrenoidosa, Chlorococcum littorale, Cyclotella cryptica, Dunaliella salina, Dunaliella tertiolecta, Dunaliella viridis, Euglena gracilis, Isochrysis galbana, Nannochloris, Nannochloropsis salina, Navicula saprophila, Neochloris oleoabundans, Nitzschia laevis, Nitzschia alba, Nitzschia communis, Nitzschia paleacea, Nitzschia closterium, Pleurochrysis carterae, Porphyridium cruentum, Prymnesium, Pseudochoricystis ellipsoidea, Scenedesmus obliquus, Scenedesmus quadricauda, Scenedesmus acutus, Scenedesmus dimorphus, Skeletonema costatum, Spirogyra, Spirulina, Synechoccus, Amphora, Fragilaria, Schizochytrium, Rhodomonas, and genetically-engineered varieties of these and other microalgal species. It should be understood that a reason for the separation of microalgae may be to clean the carrying liquid instead or in addition to producing microalgal biomass.

An initial step in such a process is conditioning of the microalgae by mechanically rupturing the cells. Without wishing to be bound by theory, cell rupture is believed to expose hydrophobic particles or surfaces which render them amenable to collection and dewatering by an adsorptive bubble separation process. The mechanical rupture method of the process does not use or introduce chemicals into the conditioning and collection process nor does it require heating, cooling or freezing of the microalgal dispersion. The rupture of microalgae by the process hereof utilizes grinding technologies in the presence of an abrasive grinding media. Due to the nature of grinding, there are many parameters for control that allow for precise grinding.

Grinding mills are commonly used to reduce particle sizes of solid materials. These types of materials can range from minerals to pigments in dyes, to chemical solids and powders. Microalgae cells are not hard, as are minerals, and thus the energy required to rupture them is low by comparison. The physical size of the microalgae cells are also quite uniform unlike mineral slurries where a wide variation in particle sizes is normal. It is also preferred that the algae bodies are only ruptured, and not disintegrated, because smaller particles are less efficiently captured by the adsorptive bubble separation process.

In the minerals industry, ore is ground to liberate the minerals of interest from the carrying rock. Typically, these are large rotating drums with the grinding media lifted and rolled within the mills. Slurries of the carrying liquid and ore particles are introduced at one end of the drum and flow through such that they are impacted by the tumbling and rolling grinding media charge. The residence time and the probability of impact with sufficient breakage energy delivered by that impact determines the extent of grinding that takes place. These are high-energy impact, low-frequency grinding devices. These devices are useful for processing large volumes of material that are typically encountered in mining applications. In the area of fine grinding, rather than use low-frequency, high-energy impacts to perform the grinding, high-frequency (thousands of impacts per minute) low-energy impacts are used. In this method of grinding, the characteristics of the grinding media, the frequency, the amplitude, and the residence time of the material to be ground are all controlled. With these controls, it is possible to avoid over-grinding the particles, which can make the material difficult to recover.

Likewise, by precise control, the microalgae cells can be ruptured without excessive cell disintegration by the action of the grinding media, thus rendering the microalgae bodies hydrophobic, but sufficiently large to be efficiently captured by the bubbles. In this way, they can be collected onto bubbles and dewatered with an adsorptive bubble process. The precise controls offered by media grinding technologies avoids over-grinding which creates extremely small particles of cell contents which are more difficult to recover. Un-ruptured cells can also be minimized, as they may represent a loss if they are not ruptured elsewhere.

A number of grinding technologies are amenable to the conditioning step herein described. These include, but are not limited to, vibratory grinding mills, agitated bead mills, ultrasonic chambers containing grinding media and combinations thereof.

Agitated bead mills (stirred media mills) employ a chamber containing the grinding media and a agitator (stirrer) including a motor-driven rotor shaft with attached disks, blades, pins, paddles or a spiral blade. The rotor shaft may rotate at low to high speed depending on the exact mill design. The mill may be either horizontal or vertical in design. This high-energy grinding process may be performed batch-wise or continuously although continuous operation is preferred. Examples of suitable agitated bead mills include those produced by Netzsch, Selb, Del.; Eiger Machinery Inc., Grayslake, Ill.; Glen Mills Inc., Clifton, N.J.; Xstrada Technology (ISAMILL™), Brisbane, Australia; and Metso Minerals Oy (VERTIMILL™, Stirred Media Detritor Mill), Helsinki, Finland.

Another technology herein described for microalgae cell rupture is vibratory grinding. This grinding process is energy efficient, as it uses a harmonic frequency to vibrate the mill and its charge of feed and grinding media. Vibratory mills have the advantage of generating much higher impact, or grinding forces than ball mills or other similar mills which are based on the gravity force generated by falling balls or rods impacting the material to be ground. Vibratory mills are not limited by gravity and much greater impact forces can be generated by the rapid vibration of a motor-driven grinding chamber. Much larger and more frequent impacts on the material translate into faster and finer grinding. Because of the high efficiency of cell rupture, the size of the equipment needed to process a feed dispersion is much smaller than a system utilizing a motor-driven rotor.

Surprisingly, large vibratory grinding systems intended for wet grinding of large, irregular, solid particulate material such as minerals and metal ores can be modified to grind liquid dispersions of microscopic microalgae. Furthermore, it was surprisingly observed that using vibratory grinding systems with algae resulted in merely ruptured algae instead of completely disintegrated algae by using equipment that was designed to grind solid ore particles. Thus, the particle size distribution of the ruptured microalgae is sufficiently uniform that adsorptive bubble separation is an effective process for concentrating the ruptured cells and cell contents. This novel use of this vibratory grinding equipment is made possible by modification of the equipment to accommodate finer grinding media and to permit continuous liquid feed and liquid product collection. The separation of the conditioned microalgal dispersion from grinding media is accomplished by one or more ways. A screen or filter can be used to confine the media in the grinding mill (as is commonly done with solids grinding) while allowing the conditioned microalgal liquid to pass through. Unlike solids grinding, the specific gravity of the microalgal particles is close to that of the carrying liquid, while the grinding media is much heavier, thus, a vertical or upward-inclined discharge tube on the exit port of the vibratory grinding mill can be used to allow media settling and liquid overflow. This discharge section of the mill is designed so that the flow of liquid upward is slower than the flow necessary to float or carry away the denser grinding media. In this way the media solids settle back into the grinding mill while the less dense conditioned microalgal product discharges from the mill. Either or both of these methods for media and liquid product separation can be used with the modified vibratory grinding mill apparatus herein described. Additionally, some or all of the media may be allowed to exit the grinding mill to be separated in one or more pieces of equipment and then recycled to the feed side of the mill. Such separation equipment could be a filter, settling tank, hydrocyclone, centrifuge and the like.

Examples of suitable large vibratory grinding mills and their manufacturers include VIBRO-ENERGY™ grinding mills from Sweco, Florence, Ky.; VIBRA-DRUMT™ grinding mills from General Kinematics, Crystal Lake, Ill.; vibrating technologies from Carrier Vibrating Equipment, Inc., Louisville, Ky.; and Vibratory Kinetic Energy Mill from Micro Grinding Systems, Little Rock, Ark.

The vibratory grinding mill can be oriented either vertically or horizontally. In a typical horizontal design, a tubular chamber (or chambers) containing the grinding media is (are) spring-mounted on a support frame. A motor with an eccentric weight or weights is attached such that the vibration caused by rotating the weight(s) is transferred to the mill and the charge of feed and grinding media. The grinding media charge can be altered in size or amount to alter the grinding characteristics, though the charge might typically fill half of the chamber volume in the mill. Additionally, the speed of the motor and the mass of the rotating weight can be changed to alter the motion of the mill. In one properly designed operation, the grinding media charge rotates about the axis of the tube, climbing one side of the tube and cascading back to the bottom of the tube.

A vertical vibratory grinding mill is typically a vertical drum mounted on springs that is activated by a motor and eccentric weight or weights mounted to the vertical drum. In a properly designed mill the grinding media charge will circulate in a vertical manner sinking at the center and rising at the perimeter of the drum. The feed dispersion could enter at the bottom, and the conditioned dispersion can be removed from the top, having traversed the mill and thus the vibrating grinding media charge. Vibratory grinding mills may also be designed with chambers utilizing, for example, toroidal, or spiral configurations.

Vibratory grinding is very efficient, as it uses a harmonic frequency to vibrate the mill and its charge of feed and grinding media. The movement of media in a vibratory grinding mill is very small, so a high percentage of the energy is directed into the grinding effort. Once the motion generator is up to operating speed, the inertia of the rotating eccentric weights greatly reduces the power input required to maintain this speed. Consequently, very low energy input is required per unit of ground product produced. Therefore the size of equipment needed to process a feed dispersion is much smaller than a system utilizing a high speed rotating impeller. Low energy usage is imperative in the production of microalgal biomass for biofuel applications.

Vibrations in the vibratory grinding mill can be generated by a momentum device or electrically or acoustically. The vibrational frequency of the grinding mill can be varied from 50 cycles per minute to thousands of cycles per minute. Alternatively, ultrasonic waves can be used to generate the vibrations.

The vibratory grinding mill comprises a chamber filled with a solid grinding media that is vibrated. The chamber can be any shape and can be of any acceptable material of construction. Suitable materials of construction include poly(vinyl chloride) ("PVC"), high density polyethylene ("HDPE"), steel, other metals, glass, ceramics, etc. In addition, the chamber can be lined with replaceable wear resistant materials such as, but not limited to, HDPE, ceramic, steel or rubber.

The vibratory grinding mill can be operated in batch or continuous mode although continuous operation is preferred. The rupture of cells is a function of the probability of cells being impacted by the grinding media, and this is a function of the amount and size of the grinding media and the residence time that the cells are in the mill. For a continuous operation, the residence time in the vibratory grinding mill can be varied by controlling the feed rate into the mill and the volume of the chamber. If it is operated in batch mode, the residence time is a function of the operating time for a batch.

The grinding media is the substance through which the force of the mill is transmitted to the substrate to be ground. The kinetic energy stored in the media when it is moving is converted to mechanical energy when it hits the substrate. The grinding media may comprise one or more types of solids that include, but are not limited to, sand, salt, quartz, diamonds or beads, balls, rods or cylinders of any material such as but not limited to glass, plastic, ceramic, garnet, corundum, silica, alumina, zirconia, (including fused zirconium oxide, sintered zirconium silicate, high density zirconium oxide, rare earth stabilized zirconium oxide, and yttrium stabilized zirconium oxide), titania, tungsten carbide, boron carbide, agate, silicon carbide, silicon nitride, sapphire, ruby, zircon, steel, iron, magnetic particles or any material found to achieve the degree of breakage desired. The particle size of the grinding media can be quite specific or vary over a distribution of sizes. Media size can vary from very small 140/230 mesh (63-105 micron) beads to large 30 mm balls. The size depends on the characteristics of the microalgae to be broken and the type of grinding mill used. As an example, diatoms are harder than microalgae without cell walls, and thus may require different grinding media. Dunaliella sauna has a cell membrane but no cell wall so it is easier to disrupt. It is required that the grinding media impact the cells with sufficient energy to break them. Grinding media will abrade itself, and thus will reduce in size, so unless the entire grinding media charge is replaced periodically, there will be a range of sizes within the mill at any given time. Once the grinding media has become small enough to pass through a screen or to be borne by the carrying liquid, it will flow out with the discharge.

Microalgal cell rupture by the grinding methods disclosed herein produces conditioned microalgae dispersions that are especially amenable to concentration by the adsorptive bubble separation methods known in the art. As these grinding methods and adsorptive bubble separation processes can be performed with high flow rates, the invention is useful in the economical production of microalgal biomass. The invention makes use of an apparatus for adsorptive bubble separation generally known as a flotation cell.

U.S. Pat. Nos. 4,938,865 and 5,332,100, the contents of the entirety of each of which are incorporated herein by this reference, disclose an adsorptive bubble separation process and apparatus (commonly known as a "Jameson cell") wherein an aqueous-particle dispersion feed enters the top of a vertical duct (downcomer) and passes through an orifice plate to form a high velocity liquid jet. A gas, usually air introduced into the downcomer headspace, is dispersed into the mixture as the liquid jet impacts a foam column within the downcomer. The volume within the downcomer is referred to as the collection zone wherein most of the particles adsorb to the surface of the bubbles. The resulting gas-liquid-particle dispersion exits through the bottom of the downcomer into the separation zone (riser) where the bubbles separate from the tails (water and non-absorbed materials). In the separation zone, the gas-liquid-particle dispersion has sufficient residence time to allow the tiny bubbles with collected particles to coalesce (combine and enlarge) and rise to the liquid surface forming a particle-rich, floating froth in the froth zone. The froth is collected by allowing it to float outward to the perimeter of the apparatus and overflow into an open launder (collection trough). Provisions are made in these patents to incorporate froth washing in the froth zone by introducing a liquid onto the froth from above thus creating a net downward liquid flow and washing the entrained gangue (undesired solid matter) and non-adsorbed particles away from the froth. This washing produces a purer froth, and therefore a more selective separation. The utility of the Jameson flotation cell for microalgal concentration was disclosed in U.S. Pat. Nos. 5,776,349 and 5,951,875, the contents of the entirety of which are incorporated herein by this reference. In this prior art the microalgal dispersions were ruptured by the use of high pressure pumps.

In column flotation cells such as the MICROCEL™, U.S. Pat. Nos. 4,981,582 and 5,167,798; the Deister Column Cell, U.S. Pat. No. 5,078,921; and the Multistage Loop-Flow Flotation (MSTLFLO) column, U.S. Pat. No. 5,897,772 (the contents of the entirety of each of which are incorporated herein by this reference), the collection, separation, and froth zones and froth washing are combined in a tall, cylindrical tank, which is less effective and more expensive to construct. In these column flotation cells, the froth at the top of the column overflows into an outer launder that surrounds the column.

Mechanical flotation cells typically employ a rotor and stator mechanism for gas induction, bubble generation, and liquid circulation thus providing for bubble and particle collision. The ratio of vessel height to diameter, termed the "aspect ratio", usually varies from about 0.7 to 2. Typically, four or more cells each having a centrally mounted rotor and stator mechanism are arranged in series. The liquid-particle dispersion is fed into the cell and air is sucked into the cell through a hollow shaft agitator. The air stream is broken by the rotating impeller, so that small bubbles are emitted from the end of the impeller blades. An auxiliary blower may also be used to provide sufficient gas flow to the cell. Rising bubbles together with attached particles form a froth layer on the top of the liquid surface. The froth layer overflows or is skimmed off mechanically from the top. Non-floated components are withdrawn from the bottom of the cell. Mechanical flotation cells are often used in mineral processing systems, however they have the disadvantage of large space requirements and high power consumption.

For example, U.S. Pat. Nos. 4,425,232 and 4,800,017 (the contents of the entirety of which are incorporated herein by this reference) describe mechanical flotation separation utilizing a flotation cell provided with a rotor-stator assembly submerged in a slurry and in which rotor blades agitate the slurry thoroughly mixing the solids and liquid and introducing air to the mixture for aeration and generation of froth on the liquid surface. Particles of minerals attach to carrier air bubbles which are naturally buoyant and form the froth, this being the effective mechanism for mineral recovery. The floating froth is removed from the top of the slurry together with the attached mineral particles which are recovered as froth is collapsed and dewatered.

The instantly disclosed processes are applicable to microalgal aquaculture as well as naturally occurring algal blooms that may occur on either oceans, lakes or other waterways. Examples of algal blooms that occur on the ocean include but are not limited to the microalgae that produce red tide.

Processes for microalgal conditioning and concentration are further described by the aid of the following illustrative Examples.

EXAMPLES

Example 1

Continuous Microalgae Rupture Using a Vibratory Grinding Mill

Figure 2:
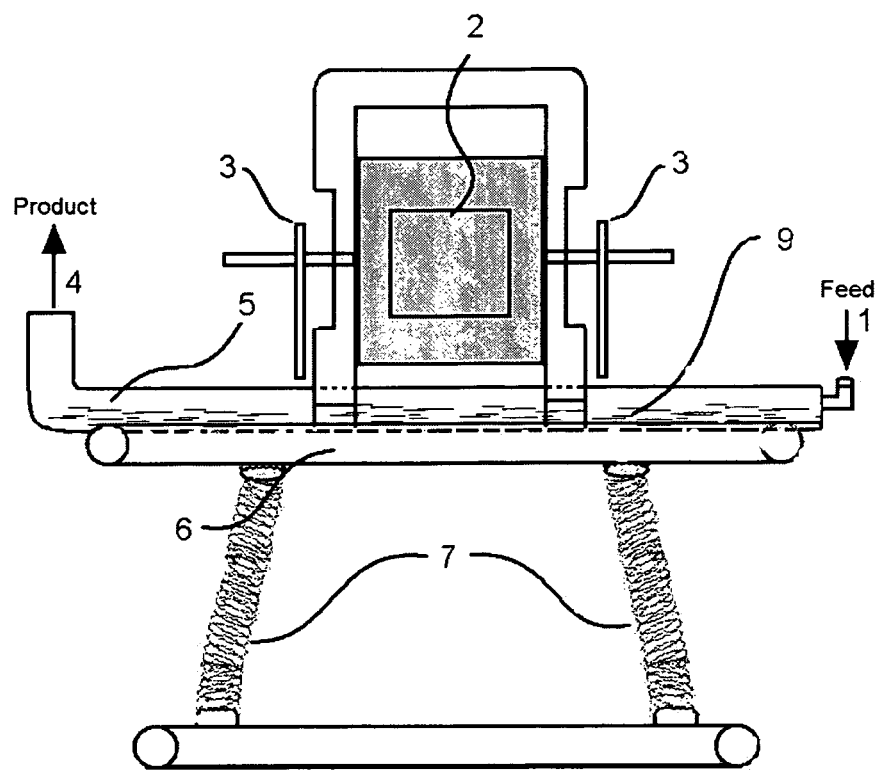
FIG. 2 is a frontal view of one possible configuration of a horizontal vibratory grinding mill. The microalgal feed dispersion enters the feed point 1 of the horizontal vibratory grinding mill 5. The mill is vibrated by the drive motor 2 with eccentric weights 3 mounted on the motor shafts. The horizontal vibratory grinding mill 5 is attached to a support frame 6 that is mounted on springs 7. The rotating action of the eccentric weights 3 causes the horizontal vibrating mill 5 and the support frame 6 to oscillate, thus vibrating the grinding media charge 9 and impacting the microalgae and breaking it. The conditioned microalgae dispersion exits from the mill discharge 4.
Figure 3:
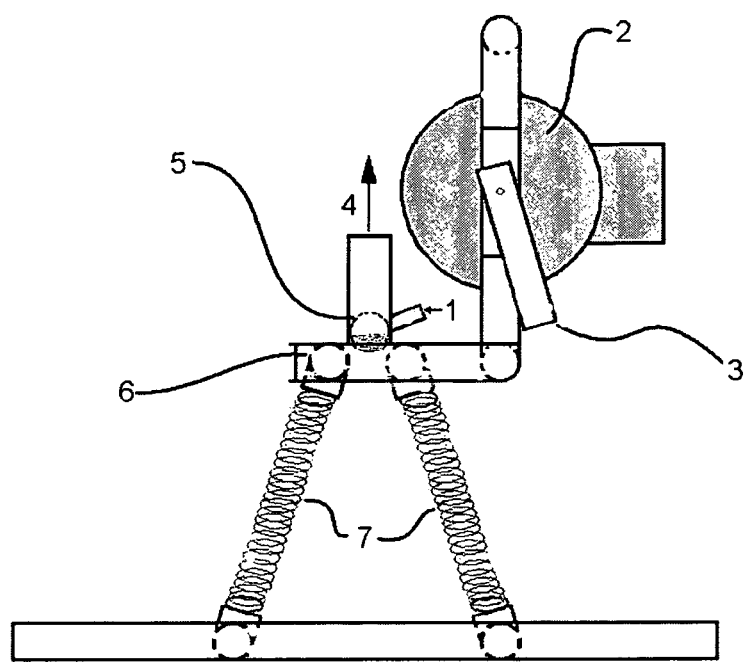
FIG. 3 is a side view of one possible configuration of a horizontal vibratory grinding mill. The mounting of the drive motor 2 and the eccentric weights 3 are clearly shown in this view.
Figure 4:
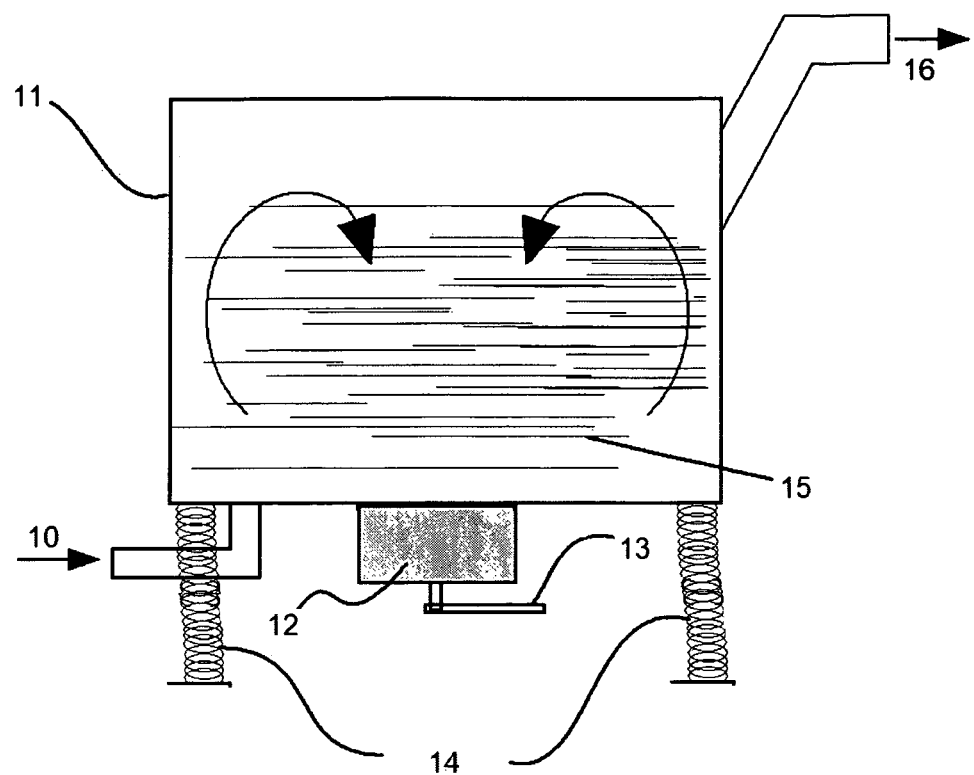
FIG. 4 is a side view of one possible configuration of a vertical vibratory grinding mill. The algal feed dispersion enters the feed point 10 of the vertical vibratory grinding mill 11. This vertical vibratory grinding mill is activated by the drive motor 12 with eccentric weight 13 mounted on the shaft. The vertical vibratory grinding mill 11 is mounted on springs 14. The rotating action of the eccentric weights 13 causes the vertical vibratory grinding mill 11 to oscillate, thus vibrating the grinding media charge 15 and impacting the microalgae and breaking it. The aqueous conditioned microalgae dispersion exits from the mill at the discharge point 16.

A series of tests were performed with both a horizontal and a vertical vibratory grinding mill. The mills were constructed of PVC pipe of 0.5-inch, 0.75-inch, and 1-inch pipe. Lengths were varied from 12 inches to 18 inches to vary the residence times. A variable-speed, gear pump was used to feed the mill with aqueous microalgae dispersions. Feed rates varied from 100 mL per minute to 300 mL per minute so as to also vary the residence times. The species of microalgae used was *Dunaliella salina*, and the feed population varied from 110,000 to 240,000 cells per mL. The horizontal configuration was similar to FIG. 2 and FIG. 3. The speed of the 1/40 horsepower motor driving the eccentric weight could be varied from 200 RPM to 5,000 RPM. The eccentric weights were varied from 20 grams to 70 grams. Silica sand of 30 grit was used as the grinding media.

The feed dispersion enters one end of the tube, and, as it travels the length of the tube, is subjected to the vibrating charge and the mixing of the cascading motion. The processed feed dispersion exits the other end of the tube. As an example of the efficiency, a residence time of 30 seconds with a vibrating frequency of 5,000 cycles per minute results in 2,500 impacts for each particle of the grinding media contained within the mill.

Microalgal cell counts using a hemacytometer and microscope were obtained on the feed into the tube and the discharge from the tube. In this series of tests, the rupture of cells varied from 11% to 43% in a single pass. Residence times within the tubes varied from 7.5 seconds to 54 seconds. Though there were numerous variables possible, the feed rate and the mill diameter were the most influential in changing the breakage rate of the microalgae. These results (Table 1) indicate that a vibratory bead mill performing at optimized residence times can achieve the desired cell rupture efficiency. The ruptured microalgal dispersion was effectively concentrated by adsorptive bubble separation in a froth flotation cell.

TABLE 1

| Test Number | Mill Configuration | Feed Rate (mL/min) | Mill Volume (cubic cm) | RPM | Residence time (seconds) | Cell Rupture |
|---|---|---|---|---|---|---|
| 1 | Horiz. | 300 | 140 | 5000 | 18.1 | 11% |
| 2 | Horiz. | 220 | 309 | 5000 | 54.8 | 13% |
| 3 | Horiz. | 200 | 245 | 5000 | 47.7 | 14% |
| 4 | Horiz. | 300 | 57 | 5000 | 7.5 | 33% |
| 5 | Horiz. | 200 | 245 | 5000 | 47.7 | 43% |
| 6 | Horiz. | 175 | 38 | 5000 | 8.5 | 26% |
| 7 | Vert. | 170 | 175 | 5000 | 18.5 | 36% |
| 8 | Vert. | 120 | 100 | 5000 | 15.0 | 11% |

Example 2

Continuous Microalgae Rupture Using an Agitated Bead Mill

Figure 5:
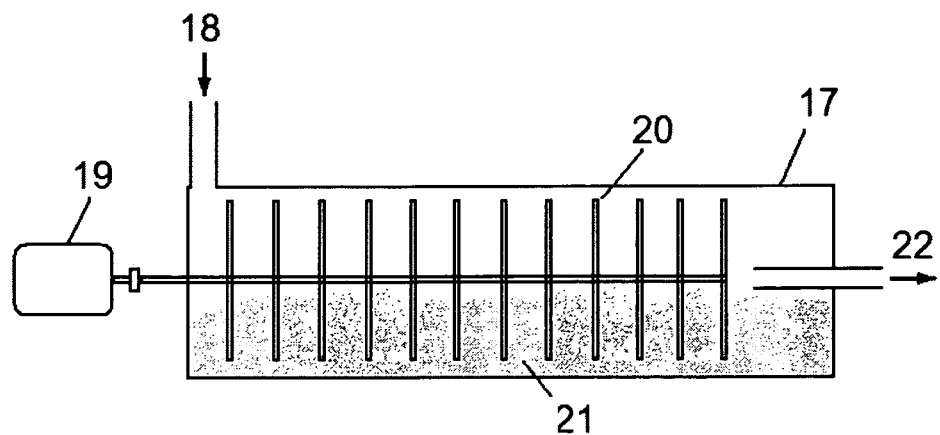
FIG. 5 is a side view of a high speed bead mill 17. The microalgal feed dispersion enters the feed point 18. Drive motor 19 rotates the disks 20 which agitates the grinding media 21 and ruptures the microalgae cells contained in the feed dispersion. The aqueous, conditioned microalgae dispersion exits from the mill at the discharge point 22.

A grinding mill utilizing the rotor-stator design of FIG. 5 was constructed using fourteen 7.25-inch (18 cm) diameter, 3/8-inch (0.95 cm) thick polypropylene disks. The disks were spaced on the rotor at 1.5-inch (3.8 cm) intervals. The mill chamber was constructed from 8-inch (20 cm) inside diameter, Schedule-40 PVC pipe, with a finished length of 40-inches (102 cm). The grinding chamber was charged with 4.5 kg of grinding media (#6 glass beads, 50/70 mesh, 210-297 microns) giving it an effective liquid volume of 9.2 liters. The disks were rotated by an electric motor at 200 RPM. The species of microalgae used was *Dunaliella salina*, and the feed population varied from 460,000 to 650,000 cells per mL. The results (Table 2) indicate that an agitated bead mill performing at optimized residence times can achieve the desired degree of cell rupture needed for adsorptive bubble separation.

TABLE 2

| Test Number | Feed Rate (mL/sec) | Residence time (minutes) | Cell Rupture |
|---|---|---|---|
| 1 | 74 | 2.1 | 55% |
| 2 | 128 | 1.2 | 49% |
| 3 | 202 | 0.76 | 11% |

Example 3

Batch Grinding of Microalgae Using a Vibratory Bead Mill

This example shows the effect of bead size in vibratory bead mill grinding of microalgae. To a 15 mL plastic test tube was added 3 mL of glass beads with 6 mL of aqueous, saline *Dunaliella salina* microalgae culture. The initial cell count for the culture was 1,540,000 cells per mL. The tube was capped and vibrated on a vortex mixer on the high setting for a period of time then a cell count was taken to assess cell rupture. The cell count versus time results are summarized in Table 3. No cell rupture occurred in the absence of beads. Data on the bead sizes is given in Table 4. This example shows the advantage of using smaller beads for faster grinding of microalgae under these conditions.

TABLE 3

| Time (min) | Bead #5 | Bead #6 | Bead #8 | Bead #10 | Bead #12 |
|---|---|---|---|---|---|
| 0.0 | 1,540,000 | 1,540,000 | 1,540,000 | 1,540,000 | 1,540,000 |
| 0.5 | 1,010,000 | 950,000 | 730,000 | 270,000 | 250,000 |
| 1.0 | 700,000 | 520,000 | 390,000 | 20,000 | 70,000 |
| 1.5 | 310,000 | 400,000 | 250,000 | 10,000 | 0 |
| 2.0 | 170,000 | 120,000 | 80,000 | 0 | 0 |
| 2.5 | 160,000 | 140,000 | 70,000 | 0 | 0 |
| 3.5 | 40,000 | 20,000 | 0 | 0 | 0 |

TABLE 4

| Bead # | Mesh | Size | Microns | Millimeters | Inches |
|---|---|---|---|---|---|
| 5 | 40/50 | Large | 297-420 | 0.297-0.420 | 0.0117-0.0165 |
| 6 | 50/70 | Medium | 210-297 | 0.210-0.297 | 0.0083-0.0117 |
| 8 | 70/100 | Medium | 149-210 | 0.149-0.210 | 0.0059-0.0083 |
| 10 | 100/170 | Fine | 88-149 | 0.088-0.149 | 0.0035-0.0059 |
| 12 | 140/230 | Extra fine | 63-105 | 0.063-0.105 | 0.0025-0.0041 |

Example 4

Batch Grinding of Microalgae Using a Vibratory Grinding Mill

This example shows the utility of the SWECO M18/5 Multiple-Chamber, Low Amplitude Vibro-Energy Grinding Mill using a ¼ HP motion generator and lead angle of 30 degrees. To a one-pint (473 ml) chamber was added 910 grams of dry glass beads and the specified amount of aqueous, saline *Dunaliella salina* microalgae culture. The cell count versus time results are summarized in Table 5.

TABLE 5

| Time (min) | Bead #5, 276 g culture | Bead #8, 292 g culture | Bead #12, 347 g culture |
|---|---|---|---|
| 0 | 200,000 | 168,000 | 198,000 |
| 0.5 | 110,000 | 110,000 | 190,000 |
| 1.0 | 89,000 | 71,000 | 163,000 |
| 1.5 | 40,000 | 35,000 | |
| 2.0 | | | 89,000 |
| 2.5 | 35,000 | 38,000 | |
| 3.0 | | | 78,000 |
| 3.5 | 26,000 | 23,000 | |
| 4.0 | | | 30,000 |

Example 5

Froth Flotation of Conditioned Microalgae Dispersion

Brine containing a 0.02% dispersion of *Dunaliella salina* was processed in an agitated bead mill as described in Example 2 to rupture the cells then treated in a Jameson flotation cell. The Jameson cell had a ratio of downcomer diameter to orifice diameter of 8.6 and a ratio of overall cell diameter to downcomer diameter of 5. The cell Jg was 0.44 cm/sec. The jet velocity was 21.5 msec. The downcomer superficial velocity was 0.20 msec and the downcomer residence time was 15.1 sec. The air to feed ratio was 0.52. The fraction of algal cell products in the froth was 0.4% on a gas-free basis.

Froth generated during the run was collected and reprocessed in the same Jameson cell to further concentrate the hydrophobic materials. The cell Jg was 0.29 cm/sec. The jet velocity was 11.9 m/sec. The downcomer superficial velocity was 0.14 msec and the downcomer residence time was 21.7 sec. The air to feed ratio was 0.49. The fraction of algal cell products in the froth was 8.3% on a gas-free basis.

Example 6

Continuous Grinding of Microalgae Using a Vibratory Grinding Mill

This Example shows the utility of the VibroKinetic Energy Grinding Mill design of Micro Grinding Systems. The test was performed in a Model 624 Laboratory Mill with a horizontal, 6-inch (15.2 cm) by 26-inch (66 cm), tubular, stainless steel, grinding chamber using a ⅝ HP vibratory motor operating at 60% power. The vibrational frequency was 1750 RPM and the orbital amplitude was ³⁄₁₆-inch (4.8 mm) resulting in a grinding force of 1290 pounds (586 kg). To the 3.2 gallon (12 liter) grinding chamber was added the specified amount of grinding media (steel rods, glass beads, sand or zirconia cylinders). About 9 liters of saline *Dunaliella salina* microalgae culture was pumped into the top of one end of the vibrating mill at a rate of 900 mL/min and allowed to exit through a screen from the bottom of the opposite end by gravity. Representative samples were taken of the feed material and the combined product of grinding. The feed was passed through the mill a total of three times. The microalgal cell count versus passes through the mill are summarized in Table 6. This example shows the effectiveness of a low-energy, vibratory grinding mill for microalgal cell rupture by achieving, for example, 95% cell rupture in three passes using glass bead grinding media.

TABLE 6

| Passes through mill | Steel rods (100 pounds) | Glass Beads, 20/30 mesh (30 pounds) | Sand, 20 mesh (27 pounds) | Zirconia, ¼" cylinders (55 pounds) |
|---|---|---|---|---|
| 0 (feed) | 1,250,000 | 860,000 | 750,000 | 880,000 |
| 1 | 520,000 | 200,000 | 250,000 | 540,000 |
| 2 | 250,000 | 70,000 | 105,000 | 460,000 |
| 3 | 160,000 | 40,000 | 10,000 | 330,000 |

What is claimed is:

1. A continuous process comprising:
   a. providing a microalgae feed dispersion comprising a carrying liquid and microalgae cells,
   b. contacting the microalgae feed dispersion with solid particles in a vibratory grinding mill to rupture the microalgae cells and form a conditioned microalgal slurry comprising hydrophobic microalgae bodies, and
   c. treating the resulting conditioned microalgal slurry with an adsorptive bubble separation process to form a stream rich in algal biomass and a stream depleted in algal biomass,
   wherein the vibratory grinding mill vibrates the microalgae feed dispersion and the solid particles.

2. The continuous process of claim 1, wherein the adsorptive bubble separation process comprises froth flotation.

3. The continuous process of claim 2, wherein the froth flotation is performed in a Jameson cell.

4. The continuous process of claim 1, further comprising: after (b), but before (c), separating the solid particles from the conditioned microalgal slurry.

5. The continuous process of claim 4, wherein the adsorptive bubble separation process comprises froth flotation.

6. The continuous process of claim 5, wherein the froth flotation is performed in a Jameson cell.

7. The continuous process of claim 1, wherein the microalgae is *Dunaliella*.

8. A continuous process comprising:
   a. providing a microalgae feed dispersion comprising a carrying liquid and *Dunaliella* microalgae cells;
   b. disrupting the cell membrane of the *Dunaliella* microalgae cells by vibrating the dispersion in the presence of solid particles to form a conditioned microalgal slurry comprising hydrophobic microalgae bodies;
   c. treating the conditioned microalgal slurry with an adsorptive bubble separation process to form a stream rich in algal biomass and a stream depleted in algal biomass.

9. The continuous process of claim 8, wherein the *Dunaliella* microalgae cells comprise *Dunaliella salina*.

10. The continuous process of claim 8, wherein the disrupting step is carried out in a vibratory grinding mill.

11. The continuous process of claim 8, wherein the adsorptive bubble separation process comprises froth flotation.

12. The continuous process of claim 11, the froth flotation is performed in a Jameson cell.

* * * * *